United States Patent

Okano et al.

[11] Patent Number: 6,030,923
[45] Date of Patent: Feb. 29, 2000

[54] LIQUID AGRICULTURAL CHEMICAL COMPOSITION

[75] Inventors: Tetsuya Okano; Keiko Hasebe; Tadayuki Suzuki; Yuichi Hioki, all of Wakayama; Tatsuo Sato, Ibaraki, all of Japan

[73] Assignees: KAO Corporation, Tokyo, Japan; Monsanto Company, St. Louis, Mo.

[21] Appl. No.: 09/051,771
[22] PCT Filed: Nov. 7, 1996
[86] PCT No.: PCT/JP96/03257
   § 371 Date: Apr. 20, 1998
   § 102(e) Date: Apr. 20, 1998
[87] PCT Pub. No.: WO97/16969
   PCT Pub. Date: May 15, 1997

[30] Foreign Application Priority Data

Nov. 7, 1995 [JP] Japan ................................. 7-289033

[51] Int. Cl.$^7$ .................................................. A01N 57/02
[52] U.S. Cl. ........................................... 504/116; 504/206
[58] Field of Search ...................... 504/206, 116

[56] References Cited

U.S. PATENT DOCUMENTS

| | | | |
|---|---|---|---|
| 4,159,901 | 7/1979 | Beestman et al. | 71/86 |
| 5,430,005 | 7/1995 | Kassebaum et al. | 504/206 |

*Primary Examiner*—S. Mark Clardy
*Attorney, Agent, or Firm*—Birch, Stewart, Kolasch & Birch, LLP

[57] ABSTRACT

A liquid agricultural chemical composition which is excellent in liquid stability even though it contains an agricultural chemical at a high concentration comprises (a) a water-soluble agricultural chemical, (b) a cationic surfactant represented by formula (I), and (c) an acid salt of a compound represented by formula (II):

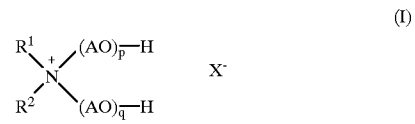

(I)

wherein $R^1$ represents an alkyl or alkenyl group having 6 to 30 carbon atoms, $R^2$ represents a hydrogen atom, a methyl group or an ethyl group, each AO represents an oxyethylene group or an oxypropylene group, each of p and q is a number of 1 to 15 with the proviso that the total of p and q is from 2 to 25, and $X^-$ represents a counter ion; and

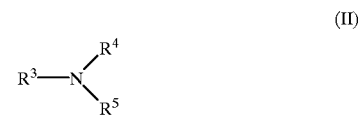

(II)

where $R^3$ represents an alkyl or alkenyl group having 4 to 18 carbon atoms, and $R^4$ and $R^5$ represent each a hydrogen atom, a methyl group, or an ethyl group.

12 Claims, No Drawings

LIQUID AGRICULTURAL CHEMICAL COMPOSITION

This application is the national phase under 35 U.S.C. §371 of prior PCT International Application No., PCT/JP96/03257, which has an International filing date of Nov. 7, 1996, which designated the United States of America, the entire contents of which are hereby incorporated by reference.

BACKGROUND OF THE INVENTION

1. Field of the Invention

The present invention relates to novel liquid agricultural chemical compositions and novel adjuvant compositions for agricultural chemicals.

2. Description of the Related Art

Agricultural chemicals including insecticides, fungicides (or bactericides), herbicides, miticides (or acaricides) and plant growth regulators have been used in various dosage forms, and one example thereof includes a liquid formulation comprising a water-soluble agricultural chemical. In such a liquid formulation, it is desirable that the concentration of the agricultural chemical is as high as possible. However, it is difficult to say that the concentrations of the agricultural chemicals of the liquid agricultural chemical formulations which are now commercially available are satisfactorily high.

It has been attempted to use an inorganic salt(s) as a component of a liquid agricultural chemical formulation, together with a surfactant(s) etc., for the purpose of enhancing the activities of agricultural chemicals. However, in such a liquid agricultural chemical formulation, the chemical interaction between the agricultural chemical or the surfactant and the inorganic salt occurs, thereby salting out the agricultural chemical or the surfactant in some cases. Thus, it has been difficult to prepare a uniform and stable liquid formulation containing an inorganic sat.

An aqueous herbicide composition, which is free from such a problem, in other words, suffers from no salting out, and is stable, is disclosed in Japanese Patent Publication-B No. 7-2608 (published on Jan. 18, 1995) and European Patent Publication-A No. 274,369 (published on Jul. 13, 1988) corresponding thereto. These patent documents describe a composition comprising a water-soluble Glyphosate salt as an agricultural chemical, a quaternary ammonium salt as a surfactant and ammonium sulfate as an inorganic salt, and that the composition of this combination is stable. However, this composition is still insufficient from the viewpoint of the concentration of the agricultural chemical, and salting out occurs in cases when both the inorganic salt and the agricultural chemical are contained in large amounts.

DISCLOSURE OF THE INVENTION

Summary of the Invention

The object of the present invention is to provide a liquid agricultural chemical composition which contains an agricultural chemical at a high concentration and is excellent in stability.

Another object of the present invention is to provide a method for converting a certain agricultural chemical composition into a stable liquid.

Still another object of the present invention is to provide an adjuvant composition for agricultural chemicals which is useful in the preparation of a liquid agricultural chemical composition.

The present inventors have extensively studied to attain the above-mentioned objects. As a result of the studies, they have found that a liquid agricultural chemical composition which contains an agricultural chemical at a high concentration and which is excellent in stability, can be prepared by using an agricultural chemical, a specific cationic surfactant having the excellent effect of enhancing the efficacy of the agricultural chemical, and a specific acid salt of an amine salt. Further, they have found that even when such the agricultural chemical composition also contains an inorganic salt, the stability thereof can also be retained. The present invention has been completed on the basis of these findings.

Thus, the first embodiment of the present invention is a liquid agricultural chemical composition (i) comprising (a) a water-soluble agricultural chemical, (b) a cationic surfactant represented by formula (I), and (c) an acid salt of a compound represented by formula (II):

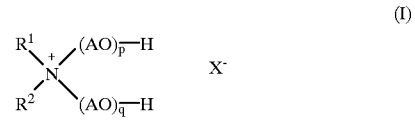

(I)

wherein $R^1$ represents a straight-chain or branched, alkyl or alkenyl group having 6 to 30 carbon atoms, $R^2$ represents a hydrogen atom, a methyl group or an ethyl group, AO may be the same or different from one another and each represents an oxyethylene group or an oxypropylene group, p and q each means an average value and is a number of 1 to 15 with the proviso that the total of p and q is from 2 to 25, and $X^-$ represents a counter ion; and

(II)

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

This agricultural chemical composition (i) preferably contains component (a) in an amount of from 35 to 85% by weight based on the entire weight of the composition.

Further, the second embodiment of the present invention is directed to a liquid agricultural chemical composition (ii) comprising (a) a water-soluble agricultural chemical, (b') a cationic surfactant represented by formula (I-a), (c) an acid salt of a compound represented by formula (II), and (d) a water-soluble inorganic salt:

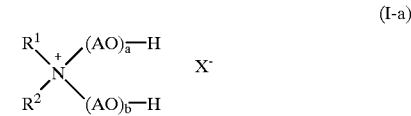

(I-a)

wherein $R^1$ represents a straight-chain or branched, alkyl or alkenyl group having 6 to 30 carbon atoms, $R^2$ represents a hydrogen atom, a methyl group or an ethyl group, AO may be the same or different from one another and each represents an oxyethylene group or an oxypropylene group, a and b each means an average value and is a number of 1 to 10 with the proviso that the total of a and b is from 2 to 15, and X⁻ represents a counter ion; and

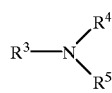
(II)

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

The agricultural chemical composition (ii) preferably contains component (a) in an amount of from 35 to 70% by weight based on the entire weight of the composition.

In this description and claims, the term "liquid" means to aqueous fluid. More specially, the concept of the "liquid" in the present invention includes not only transparent aqueous solutions but also, e.g., emulsions and turbid ones, as long as separation and sedimentation are not observed and fluidity is retained. Accordingly, the agricultural chemical composition of the present invention contains also water.

In the above-mentioned liquid agricultural chemical compositions (i) and (ii), the weight ratio of component (b) or (b') to component (c) [(b) or (b')/(c)] is preferably from 9/1 to 1/9.

The agricultural chemical is preferably a herbicide.

Furthermore, the third embodiment of the present invention is a method for converting a composition (1) comprising (a) a water-soluble agricultural chemical and (b) a cationic surfactant represented by the above formula (I) into a stable liquid, which comprises adding (c) an acid salt of a compound represented by the above formula (II) to the composition (1).

In addition, the fourth embodiment of the present invention is a method for converting a composition (2) comprising (a) a water-soluble agricultural chemical, (b') a cationic surfactant represented by the above formula (I-a) and (d) a water-soluble inorganic salt into a stable liquid, which comprises adding (c) an acid salt of a compound represented by the above formula (II) to the composition (2).

The fifth embodiment of the present invention is an adjuvant composition for agricultural chemicals comprising (b) a cationic surfactant represented by the above formula (I), and (c) an acid salt of a compound represented by the above formula (II).

The sixth embodiment of the present invention is an adjuvant composition for agricultural chemicals comprising (b') a cationic surfactant represented by the above formula (I-a), (c) an acid salt of a compound represented by the above formula (II), and (d) a water-soluble inorganic salt.

Further scope and applicability of the present invention will become apparent from the detailed description and examples given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description and these examples.

DETAILED DESCRIPTION OF THE INVENTION

First, each component of the present invention will be illustrated.

Compound (a)

The term, "an agricultural chemical" to be used in this description and claims refers to a compound which is used as an active component in usual agricultural chemical compositions or agricultural preparations. Examples thereof include a fungicide (or a bactericide), an insecticide, a miticide (or an acaricide), a herbicide and a plant growth regulator.

The agricultural chemical to be used in the present invention is water-soluble. "Water-soluble" means that its solubility in water at 25° C. is 5% or above. Further, agricultural chemicals of which the formulations are generally marketed in the form of a liquid formulation [see Noyaku Handobukku (Agricultural Chemical Handbook) 1994, published by Nippon Shokubutso Boeki Kyokai)] are also included in the scope of the water-soluble agricultural chemicals of the present invention.

Next, specific examples of the water-soluble agricultural chemicals to be used in the agricultural chemical composition of the present invention will be cited, though the water-soluble agricultural chemicals in the present invention are not restricted thereto.

Examples of fungicides include Ambam [diammonium ethylenebis(dithiocarbamate)], Thiabendazole [2-(4-thiazolyl)benzoimidazole], Iminoctadine acetate [1,1'-iminiodi(octamethylene)diguanidium triacetate], Dimethylymol (5-butyl-2-dimethylamino-6-methyl-pyrimidin-4-ol), Propamocarb hydrochloride [propyl 3-(dimethylamino) propylcarbamate hydrochloride] and Hydroxyisoxazole (3-hydroxy-5-methylisoxazole).

Examples of herbicides include dipyridyl herbicides, diazine herbicides, benzoic acid herbicides, phenoxy herbicides, organophosphorus herbicides and aliphatic herbicides. Specific examples of the dipyridyl herbicides include Paraquat (1,1'-dimethyl-4,4'-bipyridinium dichloride) and Diquat (6,7-dihydrodipyrido[1,2-a: 2',1'-c] pyrazinediium dibromide). Specific examples of the diazine herbicides include Bentazon (3-isopropyl-3H-2,1,3-benzothiadiazin-4-one-2,2-dioxide) and salts thereof (e.g., its sodium salt). specific examples of the benzoic acid herbicides include MDBA (dicamba) (3,6-dichloro-2-methoxybenzoic acid dimethylamine salt) and Imazapyr [isopropylammonium (RS)-2-(4-isopropyl-4-methyl-5-oxo-2-imidazolin-2-yl)nicotinate]. Specific examples of the phenoxy herbicides include 2,4-D sodium salt (sodium 2,4-dichlorophenoxyacetate), MCP (2-methyl-4-chlorophenoxyacetic acid) and salts thereof (e.g., its sodium salt). MCPP [d,1-2-(4-chloro-o-tolyloxy)propionic acid] and salts thereof (e.g., its potassium salt), and Triclopyr (3,5,6-trichloro-2-pyridyloxyacetic acid) and salts thereof (e.g., its triethylamine salt). Specific examples of the organophosphorus herbicides include Glyphosate [N-(phosphonomethyl)glycine] and water-soluble salts thereof, Bialophos [sodium salt of L-2-amino-4-[(hydroxy)(methyl) phosphinoyl]butyryl-L-alanyl-L-alanine] and Glufosinate (ammonium DL-homoalanin-4-yl(methyl)phosphinate). Further, a specific example of the aliphatic herbicides includes Tetrapione (sodium 2,2,3,3-tetrafuluoropropionate).

Furthermore, examples of plant growth regulators include MH (maleic hydrazide), Ethrel (2-chloroethylphosphonic acid), UASTA and Bialophos.

Herbicides are preferred as the agricultural chemicals to be used in the agricultural chemical composition of the present invention. Among the herbicides described above, organophosphorus herbicides, in particular, Glyphosate [N-(phosphonomethyl)glycine] and water-soluble salts thereof, Bialophos [sodium salt of L-2-amino-4-[(hydroxy)(methyl) phosphinoyl]butyryl-L-alanyl-L-alanine] and Glufosinate [ammonium DL-homoalanin-4-yl(methyl)phosphinate] are preferred.

Compounds (b) and (b')

The agricultural chemical composition, and the adjuvant composition for agricultural chemicals of the present invention contains the cationic surfactant represented by the above formula (I) [i.e., component (b)]. Such a cationic surfactant exerts the excellent effect of enhancing the efficacy of the agricultural chemical.

Among the compounds represented by formula (I) according to the present invention, those represented by formula (I) wherein $R^1$ is a straight-chain or branched, alkyl or alkenyl group having 8 to 24, particularly 8 to 20, carbon atom are preferred. The (poly)oxyalkylene groups [i.e., $(AO)_p$ and $(AO)_q$] each consists of at least one oxyethylene group and/or at least one oxypropylene group. It is preferable that p and q, which represent the average numbers of the oxyalkylene groups, may be the same or different from each other and are each a number of 1 to 12 and that the total of p and q (i.e., the average number of the oxyalkylene groups per molecule) is a number of 2 to 20.

When the agricultural chemical composition and the adjuvant composition for agricultural chemicals of the present invention contains component (d), as will be described hereinafter, use is made of the cationic surfactant represented by the above formula (I-a) [i.e., component (b')] instead of component (b).

Among the compounds represented by the formula (I-a) according to the present invention, those represented by formula (I-a) wherein $R^1$ is a straight-chain or branched, alkyl or alkenyl group having 8 to 24, particularly 8 to 20, carbon atoms are preferred. The (poly)oxyalkylene groups [i.e., $(AO)_a$ and $(AO)_b$] each consists of at least one oxyethylene group and/or at least one oxypropylene group. It is preferable that a and b, which represent the average numbers of the oxyalkylene groups, may be the same or different from each other and are each a number of 1 to 8, particularly 1 to 5 and that the total of a and b (i.e., the average number of the oxyalkylene groups per molecule) is a number of 2 to 10.

Further, examples of the counter ion $X^-$, in formulae (I) and (I-a) include halide anions such as $Cl^-$, $Br^-$ and $I^-$, alkylsulfate anions.

When employed together with an agricultural chemical, the cationic surfactants represented by the above formulae (I) and (I-a) according to the present invention can enhance the efficacy of the agricultural chemical.

Component (c)

The agricultural chemical composition of the present invention further contains (c) an acid salt of the amine compound represented by the above formula (II), in addition to component (a) and component (b) or (b') described above. Further, the adjuvant composition for agricultural chemicals of the present invention contains further (c) an acid salt of the compound represented by the above formula (II), in addition to component (b) or (b') described above. By using such the acid salt of such an amine, the amount of the agricultural chemical can be enhanced.

Among acid salts of the compounds represented by the above formula (II), acid salts of those represented by formula (II) wherein $R^3$ is an alkyl or alkenyl group having 6 to 18, particularly 6 to 14, carbon atoms are preferred. Acid salts of those represented by formula (II) wherein $R^4$ and $R^5$ are each a hydrogen atom or a methyl group are also preferred.

In the present invention, the amine compound represented by formula (II) is used in the form of an acid salt thereof, in view of handling thereof. Such an acid salt can be prepared by treating the amine compound represented by formula (II) with an inorganic acid such as hydrochloric acid, sulfuric acid, nitric acid and phosphoric acid, or an organic acid such as acetic acid.

Compound (d)

Among the liquid agricultural chemical compositions of the present invention, those comprising component (b') further contain (d) a water-soluble inorganic salt(s). Further, among the adjuvant compositions of the present invention, those comprising component (b') further contain (d) a water-soluble inorganic salt(s).

Examples of inorganic salts include inorganic ammonium salt such as ammonium sulfate, ammonium nitrate, ammonium phosphate, ammonium thiocyanate, ammonium chloride and ammonium sulfamate; potassium dihydrogenphosphate; dipotassium hydrogenphosphate; sodium dihydrogenphosphate; disodium hydrogenphosphate; and sodium carbonate; among which inorganic ammonium salts are preferred. When the agricultural chemical composition also contains the water-soluble inorganic salt (d), the efficacy of the agricultural chemical can be further enhanced.

The liquid agricultural chemical composition (i) of the first embodiment of the present invention comprises the above-mentioned components (a), (b) and (c). This agricultural chemical composition usually contains water as well, and can be prepared by, for example, dissolving components (a), (b) and (c) in water. Although the amounts of components (a), (b) and (c) and water of the liquid agricultural chemical composition according to the first embodiment of the present invention are not particularly restricted, it is preferable that they are each added in the amounts as described below, based on the entire weight of the composition:

Component (a): preferably 35 to 85% by weight, still more preferably 45 to 75% by weight, Component (b): preferably 0.35 to 30% by weight, still more preferably 0.7 to 20% by weight, Component (c): such an amount that the weight ratio, (b)/(c), is in the range of preferably from 9/1 to 1/9, still more preferably 8/2 to 2/8, and Water: the balance.

The liquid agricultural chemical composition (ii) of the second embodiment of the present invention comprises the above-mentioned components (a), (b'), (c) and (d). This agricultural chemical composition usually contains water as well, and can be prepared by, for example, dissolving components (a), (b'), (c) and (d) in water. Although the amounts of components (a), (b'), (c) and (d), and water of the liquid agricultural chemical composition according to the second embodiment of the present invention are not particularly restricted, it is preferable that they are each added in the amounts as described below, based on the entire weight of the composition:

Component (a): preferably 35 to 70% by weight, still more preferably 35 to 60% by weight, Component (b'): preferably 0.5 to 5% by weight, still more preferably 0.7 to 3.5% by weight, Component (c): such an amount that the weight ratio, (b')/(c), is in the range of preferably from 9/1 to 1/9, still more preferably 8/2 to 2/8, Component (d): preferably 5 to 40% by weight, still more preferably 8 to 20% by weight, and Water: the balance.

Thus, according to the present invention, it is possible to elevate the concentration of component (a), i.e., the agricultural chemical, as compared with those of the conventional liquid agricultural chemical compositions. In addition, in the liquid agricultural chemical composition (ii) also containing component (d), i.e., the inorganic salt, it is also possible to elevate the concentration of component (d), as compared with the conventional inorganic salt containing composition. However, the concept of the agricultural chemical composition according to the present invention also includes agricultural chemical compositions having a low concentration of the agricultural chemical which can be applied as such to the crops.

The agricultural chemical composition of the present invention may further contain a surfactant other than components (b) and (b'). Examples of the surfactants capable of being used with component (b) or (b') include nonionic surfactants.

Specific examples of the nonionic surfactants include polyoxyethylene alkyl ethers, polyoxyethylene alkyl aryl ethers, condensates of polyoxyethylene alkyl aryl ethers and formaldehyde, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, esters of polyoxyalkylene block copolymers and alkyl glycerols, polyoxyalkylene alkyl sulfonamides, polyoxyalkylene rosin esters, polyoxypropylene block copolymers, polyoxyethylene oleyl ethers, polyoxyalkylene alkyl phenols, alkyl glycosides, alkyl polyglycosides and polyoxyalkylene alkyl polyglycosides, and one of them or a mixture of two or more of them is used in the present invention.

When these nonionic surfactants are also used, the amount thereof is such that the weight ratio of component (b) or (b') to the nonionic surfactant is in the range of preferably from 9.1/0.9 to 0.9/9.1, and still more preferably from 8.3/1.7 to 5/5.

The agricultural chemical composition of the present invention may also contain a chelating agent, a pH regulator and/or a thickener at need, as long as the stability thereof is not deteriorated thereby.

Examples of the chelating agents to be used in the agricultural chemical composition of the present invention include those based on aminopolycarboxylic acids, aromatic and aliphatic carboxylic acids, amino acids, ether polycarboxylic acids, phosphonic acids such as iminodimethylphosphonic acids (IDP) and alkyldiphosphonic acids (ADPA), hydroxycarboxylic acids and polyelectrolytes (including oligoelectrolytes); and dimethylglyoxime (DG). These chelating agents may be each as such, i.e., in the form of a free acid, or in the form of a salt such as a sodium salt, a potassium salt and an ammonium salt.

Specific examples of the aminopolycarboxylic acid chelating agent include:

a) compounds represented by the formula:

$RNX_2$, b) compounds represented by the formula:

$NX_3$, c) compounds represented by the formula:

R—NX—CH$_2$CH$_2$—NX—R, d) compounds represented by the formula:

R—NX—CH$_2$CH$_2$—NX$_2$, e) compounds represented by the formula:

X$_2$N—R'—NX$_2$, and compounds which are similar to compounds (e) and each has more than 4 Xs, for example, a compound represented by the formula:

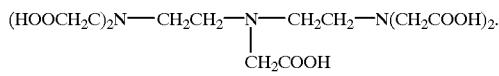

In the above formulas, X represents —CH$_2$COOH or —CH$_2$CH$_2$COOH; R represents any group constituting known chelating agents of this type, for example, a hydrogen atom, an alkyl group, a hydroxyl group or a hydroxyalkyl group; and R' represents any group constituting known chelating agents of this type, for example, an alkylene group or a cycloalkylene group.

Representative examples of the aminopolycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl) ethylenediaminetriacetic acid (EDTA-OH) and glycol ether diaminetetraacetic acid (GEDTA), and salts thereof.

Examples of the aromatic and alipatic carboxylic acid chelating agents to be used in the present invention include oxalic acid, succinic acid, pyruvic acid and anthranilic acid, and salts thereof. Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include compounds represented by the following formula, analogs of them and salts thereof (such as sodium salts thereof):

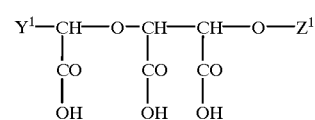

wherein Y$^1$ represents a hydrogen atom, —CH$_2$COOH or —COOH; and Z$^1$ represents a hydrogen atom, —CH$_2$COOH or

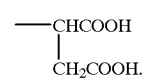

Examples of the hydroxy carboxylic acid chelating agents to be used in the present invention include malic acid, citric acid, glycollic acid, gluconic acid, heptonic acid and tartaric acid, and salts thereof.

Examples of the polyelectrolyte (including oligoelectrolyte) chelating agents to be used in the present invention include polyacrylic acid, polymaleic anhydride, α-hydroxyacrylic acid polymer, polyitaconic acid, copolymers comprising two or more of the monomers constituting these polymers, and epoxysuccinic acid polymer.

Examples of the pH regulators to be used in the present invention include citric acid, phosphoric acids (e.g., pyrophosphoric acid) and gluconic acid, and salts thereof.

Examples of the thickeners to be used in the present invention include natural, semi-synthetic and synthetic water-soluble thickeners. Specific examples of the natural mucilages usable as the natural thickeners include xanthan gum and Xanfloo derived from microorganisms, and pectin, acacia and guar gum derived from vegetables. Examples of the semisynthetic thickeners include methylated, carboxyalkylated and hydroxyalkylated celluloses, such as methylcellulose, carboxymethylcellulose and hydroxymethylcellulose; methylated, carboxyalkylated and hydroxyalkylated starch derivatives; and sorbitol. Further, examples of the synthetic thickeners include polyacrylates, polymaleates, polyvinylpyrrolidones and adducts of pentaerythritol with ethylene oxide.

The agricultural chemical composition of the present invention may further contain at least one member selected from the group consisting of plant growth regulators other than those described as the specific examples of the plant growth regulators in the illustration of component (a), fertilizers and preservatives.

The agricultural chemical composition of the present invention is used after diluting with water or as such.

The agricultural chemical composition of the present invention is used in order to control fungi (or bacteria), insects, mites (or acarids) and herbs or to regulate the growth of plants.

The third embodiment of the present invention relates to a method for converting a composition (1) containing components (a) and (b) into a stable liquid, which comprises adding component (c) to the composition (1); and the fourth embodiment of the present invention relates to a method for converting a composition (2) containing components (a), (b') and (d) into a stable liquid, which comprises adding component (c) to the composition (2).

The concept of the stabilization of the composition (1) or (2) by adding component (c) thereto includes (i) a method comprising adding component (c) as one component of the desired composition to water together with other component (s) in the preparation of the desired composition, (ii) a method comprising preparing a desired composition by using a mixture of component (b) or (b') and component (c) which has been preliminarily prepared, and (iii) a method comprising adding component (c) to the composition (1) or (2) which has been prepared.

By adding component (c), the stability of composition (1) containing components (a) and (b) is improved. The effect of improving the stability of a liquid by component (c) is satisfactorily exhibited even when a component such as water-soluble inorganic salts [component (d)] which deteriorates the stability of the liquid, e.g., a solution, is added to the composition [for example, a case of using the composition (2)]. "The improvement of the stability of a liquid" herein means that, for example, the separation of a liquid to two or more layers (or phases) or the formation of sedimentation from a liquid can be prevented. Due to no occurrence of layer separation and sedimentation, a lot of advantages including, e.g., the prevention of separation and/or sedimentation during transportation of the agricultural chemical composition, and the ease of dilution of the agricultural chemical composition, can be brought about by the present invention.

The present invention also relates to an adjuvant composition for agricultural chemicals comprising components (b) and (c), and an adjuvant composition for agricultural chemicals comprising components (b'), (c) and (d). Each of components (b), (b') and (d) can enhances the efficacies of agricultural chemicals. Component (c) contributes to the improvement in the stability of a system where both an agricultural chemical and component (b) or (b') are present, or other systems where components (b') and (d) are present.

The form of the adjuvant composition for agricultural chemicals according to the present invention is not restricted, and the composition may be a liquid, a solid (e.g., a powder), a suspension or the like. The adjuvant composition for agricultural chemicals of the present invention may contain other additive(s) such as solvents, emulsifiers, dispersants and carriers, depending upon the formulation or form thereof.

The adjuvant composition for agricultural chemicals according to the present invention is employed with an agricultural chemical composition which is put on the market generally in the form of a preparation. The liquid formulation containing an agricultural chemical and the active components of the adjuvant composition for agricultural chemicals according to the present invention is prepared by, for example, any of 1) a method comprising mixing an agricultural chemical composition with an adjuvant composition for agricultural chemicals, and suitably diluting the resultant mixture with water; 2) a method comprising adding an adjuvant composition for agricultural chemicals to an agricultural chemical composition having been diluted with water; and 3) a method comprising diluting an adjuvant composition for agricultural chemicals with water to give a dilution and then diluting an agricultural chemical composition with the use of the dilution.

The above-mentioned agricultural chemical composition of the present invention, the dilution of the agricultural chemical composition, the liquid formulation containing an agricultural chemical and the active components of the adjuvant composition for agricultural chemicals according to the present invention are applied to plants, cereals, vegetables, fruits, trees, fruit trees, grasses, weeds and seeds, and, at the same time, fungi, bacteria, insects, mites and acarids, by a method such as spraying. In other words, they are applied to a locus shch as a farm, a field, a plantation, a fruit garden, an orchard, a flower garden, a lawn, a wood and a forest.

According to the present invention, a liquid agricultural chemical composition, which is excellent in liquid stability, particularly in liquid stability when the liquid suffers from temperature changes, even though the liquid contains an agricultural chemical at a high concentration, can be obtained. Further, according to the present invention, it can be possible to prepare a stable, liquid agricultural chemical composition, even though the composition contains an agricultural chemical in a large amount. Furthermore, it can be possible to prepare a stable, liquid agricultural chemical composition which does not suffer from salting out, even though the composition contains an agricultural chemical and an inorganic salt in large amounts. In addition, by using the adjuvant composition for agricultural chemicals of the present invention, the enhancement of the efficacy of an agricultural chemical and the stabilization of a liquid formulation containing an agricultural chemical and the active components of the adjuvant composition for agricultural chemicals according to the present invention, can be attained simultaneously.

EXAMPLES

The present invention will now be described in more detail by referring to the following Examples which should not be thought of as limiting the scope of the present invention.

Example 1

Glyphosate acid (N-phosphonomethylglycine) was synthesized by a known method. Then, the Glyphosate acid was neutralized with each of isopropylamine, ammonia, monomethylamine and dimethylamine for converting it into a water-soluble salt thereof. By using Glyphosate salts thus prepared, various liquid herbicide compositions having the compositions shown in Table 1 were prepared.

With respect to each of the liquid herbicide compositions thus prepared, the conditions (conditions at a room temperature immediately after the preparation) of the compositions were observed with the naked eye. Next, only the compositions, which were in the state of one solution and trasparent immediately after the preparation thereof, were subjected to a stability test. The stability test was effected by storing the compositions in a thermostatic chamber of $-5°$ C. or $60°$ C. for one month, taking out the compositions from the thermostatic chamber, leaving them to stand under room temperatures until they exhibited a room temperature, and then observing the conditions of the compositions with the naked eye.

Table 1 shows the results.

As Table 1 shows, there is understood that the liquid herbicide compositions of the present invention are excellent in the conditions immediately after the preparation thereof, as compared with comparative products, and are also excellent in the stability in storage at a high temperature and a low temperature. On the other hand, since all of the comparative products were separated into 2 phases immediately after the preparation thereof, they could not be subjected to the stability test.

Further, weeding tests were effected in the following manner with the use of the liquid herbicide compositions of the present invention shown in Table 1, and a commercial product. Specially, the liquid herbicide compositions of the present invention and a commercially available Glyphosate herbicide were each diluted with water in such a manner that the concentration of the active component (i.e., the Glyphosate salt), calculated in terms of Glyphosate acid, would be a definite one. With the use of each of the dilutions thus prepared, weeding tests to crabgrass and cabbage were conducted. As a result, the liquid herbicide compositions of the present invention exhibited the effects of weeding comparable or superior to that of the commercial product.

TABLE 1

| | | | Invention product 1 | Comparative product 1 | Invention product 2 | Comparative product 2 | Invention product 3 | Comparative product 3 |
|---|---|---|---|---|---|---|---|---|
| Composition (wt. %) | Component (a) | Glyphosate isopropylamine salt | 60.7 | 60.7 | — | — | — | — |
| | | Glyphosate diammonium salt | — | — | 54.1 | 54.1 | — | — |
| | | Glyphosate monomethylamine salt | — | — | — | — | 53.3 | 53.3 |
| | | Glyphosate dimethylamine salt | — | — | — | — | — | — |
| | Component (b) | methylbis(2-hydroxyethyl)-coacoalkylammonium chloride | 2.5 | 6.5 | 2.5 | 3.5 | — | — |
| | | POE(5) monomethylmonococoalkyl-ammonium chloride | — | — | — | — | 2.5 | 3.5 |
| | | POE(8) monomethylmonococoalkyl-ammonium chloride | — | — | — | — | — | — |
| | Component (c) | octylamine hydrochloride | 1.0 | — | 1.0 | — | — | — |
| | | dimethyldecylamine hydrochloride | — | — | — | — | 1.0 | — |
| | Others | POE(7) alkyl (straight-chain and branched $C_{12}$) ether | 1.0 | 1.5 | 1.0 | 1.0 | — | — |
| | | POE(9) nonyl phenyl ether | — | — | — | — | 1.0 | 1.0 |
| | | POE(6) sorbitan monolaurate | — | — | — | — | — | — |
| | | water | 34.8 | 31.3 | 41.4 | 41.4 | 42.2 | 42.2 |
| Results of evaluations | Condition of composition | | one solution transparent | separated into 2 phases deposition of crystals | one solution transparent | separated into 2 phases | one solution transparent | separated into 2 phases |
| | Stability | $-5°$ C. | stable | could not be evaluated | stable | could not be evaluated | stable | could not be evaluated |
| | | $60°$ C. | stable | could not be evaluated | stable | could not be evaluated | stable | could not be evaluated |

| | | | Invention product 4 | Comparative product 4 | Invention product A | Comparative product B | Invention product C | Comparative product A |
|---|---|---|---|---|---|---|---|---|
| Composition (wt. %) | Component (a) | Glyphosate isopropylamine salt | — | — | 62.1 | 56.7 | 60.7 | 56.7 |
| | | Glyphosate diammonium salt | — | — | — | — | — | — |
| | | Glyphosate monomethylamine salt | — | — | — | — | — | — |
| | | Glyphosate dimethylamine salt | 57.0 | 57.0 | — | — | — | — |
| | Component (b) | methylbis(2-hydroxyethyl)-coacoalkylammonium chloride | — | — | 2.0 | 7.5 | 4.5 | — |
| | | POE(5) monomethylmonococoalkyl-ammonium chloride | — | — | — | — | — | — |
| | | POE(8) monomethylmonococoalkyl-ammonium chloride | 2.5 | 3.5 | — | — | — | — |
| | Component (c) | octylamine hydrochloride | — | — | 7.5 | 7.5 | 2.0 | 15.0 |
| | | dimethyldecylamine hydrochloride | 1.0 | — | — | — | — | — |

TABLE 1-continued

|  |  |  |  |  |  |  |  |  |
|---|---|---|---|---|---|---|---|---|
|  | Others | POE(7) alkyl (straight-chain and branched C$_{12}$) ether | — | — | 0.5 | — | 1.5 | — |
|  |  | POE(9) nonyl phenyl ether | — | — | — | — | — | — |
|  |  | POE(6) sorbitan monolaurate | 1.0 | 1.0 | — | — | — | — |
|  |  | water | 38.5 | 38.5 | 27.9 | 28.3 | 31.3 | 28.3 |
| Results of evaluations | Condition of composition |  | one solution transparent | separated into 2 phases | one solution transparent | one solution transparent | one solution transparent | separated into 2 phases deposition of crystals |
|  | Stability | −5° C. | stable | could not be evaluated | stable | stable | stable | could not be evaluated |
|  |  | 60° C. | stable | could not be evaluated | stable | stable | stable | could not be evaluated |

Note: In Table 1, POE is an abbreviation for polyoxyethylene, and the figures in parentheses stand for the average numbers of oxyethylene groups per one molecule. Accordingly, with respect to compounds described in the column of component (b), the figures in parentheses stand for the total of p and q in formula (I). While, with respect to compounds described in the columns other than the column of component (b), the figures in parentheses are the same as the average numbers of ethylene oxide molecules added.

Example 2

Glyphosate acid (N-phosphonomethylglycine) was synthesized by a known method. Then, the Glyphosate acid was neutralized with each of isopropylamine, ammonia and monomethylamine for converting it into a water-soluble salt thereof. By using Glyphosate salts thus prepared, and commercially available 2,4-D sodium salt, Diquat dibromide and Glufosinate ammonium salt, various liquid herbicide compositions having the compositions shown in Tables 2 to 5 were prepared.

The liquid herbicide compositions thus prepared were each subjected to the same tests as those in Example 1. Tables 2 to 5 shows the results.

As Tables 2 to 5 shows, there is understood that the liquid herbicide compositions of the present invention are excellent in the conditions immediately after the preparation thereof, as compared with comparative products, and are also excellent in storage stability at a high temperature and a low temperature. On the other hand, since all of the comparative products separated into 2 phases immediately after the preparation thereof, they could not be subjected to the stability test.

Further, weeding tests were effected in the following manner with the use of the liquid herbicide compositions of the present invention shown in Tables 2 to 5, and commercial products. Specially, the liquid herbicide compositions of the present invention and, a Glyphosate herbicide, a 2,4-D herbicide, a Diquat herbicide and a Glufosinate herbicide which were commercially available were each diluted with water in such a manner that the concentration of the active component (i.e., the agricultural chemical) would be a definite one. The dilutions thus prepared were each applied to crabgrass and cabbage which had been grown in Wagner's pots to evaluate the effects of weeding. As a result, the liquid herbicide compositions of the present invention exhibited the effects of weeding comparable or superior to those of the commercial products.

TABLE 2

|  |  |  | Invention product 5 | Comparative product 5 | Invention product 6 | Comparative product 6 |
|---|---|---|---|---|---|---|
| Composition (wt. %) | Component (a) | Glyphosate isopropylamine salt | 40.5 | 40.5 | — | — |
|  |  | Glyphosate diammonium salt | — | — | 36.0 | 36.0 |
|  |  | Glyphosate monomethylamine salt | — | — | — | — |
|  |  | 2,4-D sodium salt | — | — | — | — |
|  |  | Diquat dibromide | — | — | — | — |
|  |  | Glufosinate ammonium salt | — | — | — | — |
|  | Component (b') | methylbis(2-hydroxyethyl)-cocoalkylammonium chloride | 2.5 | 3.5 | 2.5 | 3.5 |
|  |  | POE(5) monomethyl-monococoalkylammonium chloride | — | — | — | — |
|  |  | POE(8) monomethyl-monococoalkylammonium chloride | — | — | — | — |
|  | Component (c) | octylamine hydrochloride | 1.0 | — | 1.0 | — |
|  |  | dimethyldecylamine hydrochloride | — | — | — | — |
|  | Component (d) | ammonium sulfate | 10.0 | 10.0 | 15.0 | 15.0 |
|  |  | ammonium phosphate | — | — | — | — |
|  |  | ammonium nitrate | — | — | — | — |
|  |  | ammonium chloride | — | — | — | — |
|  | Others | POE(7) alkyl (straight-chain and branched C$_{12}$) ether | 1.0 | 1.0 | 1.0 | 1.0 |

TABLE 2-continued

|  |  |  | Invention product 5 | Comparative product 5 | Invention product 6 | Comparative product 6 |
|---|---|---|---|---|---|---|
|  |  | POE(9) nonyl phenyl ether | — | — | — | — |
|  |  | POE(6) sorbitan monolaurate | — | — | — | — |
|  |  | water | 45.0 | 45.0 | 44.5 | 44.5 |
| Results of evaluations | Condition of composition |  | one solution transparent | separated into 2 phases sedimentation was observed | one solution transparent | separated into 2 phases sedimentation was observed |
|  | Stability | −5° C. | stable | could not be evaluated | stable | could not be evaluated |
|  |  | 60° C. | stable | could not be evaluated | stable | could not be evaluated |

TABLE 3

|  |  |  | Invention product 7 | Comparative product 7 | Invention product 8 | Comparative product 8 |
|---|---|---|---|---|---|---|
| Composition (wt. %) | Component (a) | Glyphosate isopropylamine salt | — | — | — | — |
|  |  | Glyphosate diammonium salt | 42.0 | 42.0 | — | — |
|  |  | Glyphosate monomethylamine salt | — | — | 35.5 | 35.5 |
|  |  | 2,4-D sodium salt | — | — | — | — |
|  |  | Diquat dibromide | — | — | — | — |
|  |  | Glufosinate ammonium salt | — | — | — | — |
|  | Component (b') | methylbis(2-hydroxyethyl)-cocoalkylammonium chloride | 2.5 | 3.5 | — | — |
|  |  | POE(5) monomethyl-monococoalkylammonium chloride | — | — | 2.5 | 3.5 |
|  |  | POE(8) monomethyl-monococoalkylammonium chloride | — | — | — | — |
|  | Component (c) | octylamine hydrochloride | 1.0 | — | 1.0 | — |
|  |  | dimethyldecylamine hydrochloride | — | — | — | — |
|  | Component (d) | ammonium sulfate | — | — | — | — |
|  |  | ammonium phosphate | 10.0 | 10.0 | 15.0 | 15.0 |
|  |  | ammonium nitrate | — | — | — | — |
|  |  | ammonium chloride | — | — | — | — |
|  | Others | POE(7) alkyl (straight-chain and branched $C_{12}$) ether | — | — | — | — |
|  |  | POE(9) nonyl phenyl ether | 1.0 | 1.0 | — | — |
|  |  | POE(6) sorbitan monolaurate | — | — | — | — |
|  |  | water | 43.5 | 43.5 | 46.0 | 46.0 |
| Results of evaluations | Condition of composition |  | one solution transparent | separated into 2 phases sedimentation was observed | one solution transparent | separated into 2 phases sedimentation was observed |
|  | Stability | −5° C. | stable | could not be evaluated | stable | could not be evaluated |
|  |  | 60° C. | stable | could not be evaluated | stable | could not be evaluated |

TABLE 4

|  |  |  | Invention product 9 | Comparative product 9 | Invention product 10 | Comparative product 10 |
|---|---|---|---|---|---|---|
| Composition (wt. %) | Component (a) | Glyphosate isopropylamine salt | — | — | — | — |
| | | Glyphosate diammonium salt | — | — | — | — |
| | | Glyphosate monomethylamine salt | — | — | — | — |
| | | 2,4-D sodium salt | 55.0 | 55.0 | — | — |
| | | Diquat dibromide | — | — | 50.0 | 50.0 |
| | | Glufosinate ammonium salt | — | — | — | — |
| | Component (b') | methylbis(2-hydroxyethyl)-cocoalkylammonium chloride | — | — | — | — |
| | | POE(5) monomethyl-monococoalkylammonium chloride | — | — | — | — |
| | | POE(8) monomethyl-monococoalkylammonium chloride | 2.5 | 3.5 | 2.5 | 3.5 |
| | Component (c) | octylamine hydrochloride | — | — | — | — |
| | | dimethyldecylamine hydrochloride | 1.0 | — | 1.0 | — |
| | Component (d) | ammonium sulfate | — | — | — | — |
| | | ammonium phosphate | — | — | — | — |
| | | ammonium nitrate | 15.0 | 15.0 | 15.0 | 15.0 |
| | | ammonium chloride | — | — | — | — |
| | Others | POE(7) alkyl (straight-chain and branched $C_{12}$) ether | — | — | — | — |
| | | POE(9) nonyl phenyl ether | — | — | — | — |
| | | POE(6) sorbitan monolaurate | 1.0 | 1.0 | 1.0 | 1.0 |
| | | water | 25.5 | 25.5 | 30.5 | 30.5 |
| Results of evaluations | Condition of composition | | one solution transparent | separated into 2 phases | one solution transparent | separated into 2 phases |
| | Stability | −5° C. | stable | could not be evaluated | stable | could not be evaluated |
| | | 60° C. | stable | could not be evaluated | stable | could not be evaluated |

TABLE 5

|  |  |  | Invention product 11 | Comparative product 11 |
|---|---|---|---|---|
| Composition (wt. %) | Component (a) | Glyphosate isopropylamine salt | — | — |
| | | Glyphosate diammonium salt | — | — |
| | | Glyphosate monomethylamine salt | — | — |
| | | 2,4-D sodium salt | — | — |
| | | Diquat dibromide | — | — |
| | | Glufosinate ammonium salt | 43.0 | 43.0 |
| | Component (b') | methylbis(2-hydroxyethyl)-cocoalkylammonium chloride | — | — |
| | | POE(5) monomethylmonococoalkyl-ammonium chloride | 2.5 | 3.5 |
| | | POE(8) monomethylmonococoalkyl-ammonium chloride | — | — |
| | Component (c) | octylamine hydrochloride | — | — |
| | | dimethyldecylamine hydrochloride | 1.0 | — |
| | Component (d) | ammonium sulfate | — | — |
| | | ammonium phosphate | — | — |
| | | ammonium nitrate | — | — |
| | | ammonium chloride | 15.0 | 15.0 |
| | Others | POE(7) alkyl (straight-chain and branched $C_{12}$) ether | — | — |
| | | POE(9) nonyl phenyl ether | — | — |
| | | POE(6) sorbitan monolaurate | — | — |
| | | water | 38.5 | 38.5 |

TABLE 5-continued

| | | Invention product 11 | Comparative product 11 |
|---|---|---|---|
| Results of evaluations | Condition of composition | one solution transparent | separated into 2 phases |
| | Stability −5° C. | stable | could not be evaluated |
| | 60° C. | stable | could not be evaluated |

Note: In Tables 2 to 5, POE is an abbreviation for polyoxyethylene, and the figures in parentheses stand for the average numbers of oxyethylene groups per one molecule. Accordingly, with respect to compounds described in the column of component (b'), the figures in parentheses stand for the total of a and b in formula (I-a). While, with respect to compounds described in the columns other than the column of component (b'), the figures in parentheses are the same as the average numbers of ethylene oxide molecules added.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A liquid agricultural chemical composition comprising (a) a water-soluble agricultural chemical, (b) a cationic surfactant represented by formula (I), and (c) an acid salt of a compound represented by formula (II):

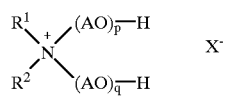
(I)

wherein $R^1$ represents a straight-chain or branched, alkyl or alkenyl group having 6 to 30 carbon atoms, $R^2$ represents a hydrogen atom, a methyl group or an ethyl group, AO may be the same or different from one another and each represents an oxyethylene group or an oxypropylene group, p and q each means an average value and is a number of 1 to 15 with the proviso that the total of p and 1 is from 2 to 25, and $X^-$ represents a counter ion; and

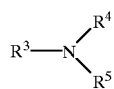
(II)

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

2. The liquid agricultural chemical composition according to claim 1, wherein the weight ratio of component (b) to component (c) {(b)/(c)} is from 9/1 to 1/9.

3. The liquid agricultural chemical composition according to claim 1, wherein the agricultural chemical is a herbicide.

4. The liquid agricultural chemical composition according to claim 1, which comprises the water-soluble agricultural chemical (a) in an amount of from 35 to 85% by weight based on the entire weight of the composition.

5. A liquid agricultural chemical composition comprising (a) a water-soluble agricultural chemical, (b') a cationic surfactant represented by formula (I-a), (c) an acid salt of a compound represented by formula (II), and (d) a water-soluble inorganic salt:

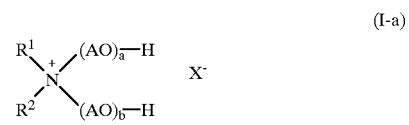
(I-a)

wherein $R^1$ represents a straight-chain or branched, alkyl or alkenyl group having 6 to 30 carbon atoms, $R^2$ represents a hydrogen atom, a methyl group or an alkyl group, AO may be the same or different from one another and each represents an oxyethylene group or an oxypropylene group, a and b each means an average value and is a number of 1 to 10 with the proviso that the total of a and b is from 2 to 15, and $X^-$ represents a counter ion; and

(II)

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

6. The liquid agricultural chemical composition according to claim 5, wherein the weight ratio of component (b') to component (c) [(b')/(c)] is from 9/1 to 1/9.

7. The liquid agricultural chemical composition according to claim 5, wherein the agricultural chemical is a herbicide.

8. The liquid agricultural chemical composition according to claim 5, which comprises the water-soluble agricultural chemical (a) in an amount of from 35 to 70% by weight based on the entire weight of the composition.

9. A method for converting a composition (1) comprising (a) a water-soluble agricultural chemical and (b) a cationic surfactant represented by formula (I) into a stable liquid, which comprises adding (c) an acid salt of a compound represented by formula (II) to composition (1):

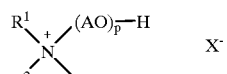

wherein $R^1$ represents a straight-chain or branched alkyl or alkenyl group having 6 to 30 carbon atoms, $R^2$ represents a hydrogen atom, a methyl group or an ethyl group, AO may be the same or different from one another and each represents an oxyethylene group or an oxypropylene group, p and q each means an average value and is a number of 1 to 15 with the proviso that the total of p and q is from 2 to 25, and $X^-$ represents a counter ion; and

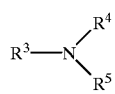

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

10. A method for converting a composition (2) comprising (a) a water-soluble agricultural chemical, (b') a cationic surfactant represented by formula (I-a) and (d) a water-soluble inorganic salt into a stable liquid, which comprises adding (c) an acid salt of a compound represented by formula (II) to composition (2):

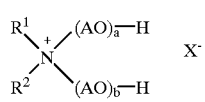

wherein $R^1$ represents a straight-chain or branched, alkyl or alkenyl group having 6 to 30 carbon atoms, $R^2$ represents a hydrogen atom, a methyl group or an ethyl group, AO may be the same or different from one another and each represents an oxyethylene group or an oxypropylene group, a and b each means an average value and is a number of 1 to 10 with the proviso that the total of a and b is from 2 to 15, and $X^-$ represents a counter ion; and

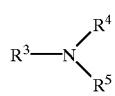

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

11. An adjuvant composition for agricultural chemicals comprising (b) a cationic surfactant represented by formula (I) and (c) an acid salt of a compound represented by formula (II):

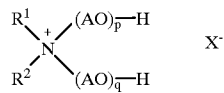

wherein $R^1$ represents a straight-chain or branched, alkyl or alkenyl group having 6 to 30 carbon atoms, $R^2$ represents a hydrogen atom, a methyl group or an ethyl group, AO may be the same or different from one another and each represents an oxyethylene group or an oxypropylene group, p and q each means an average value and is a number of 1 to 15 with the proviso that the total of p and q is from 2 to 25, and $X^-$ represents a counter ion; and

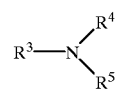

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

12. An adjuvant composition for agricultural chemicals comprising (b') a cationic surfactant represented by formula (I-a), (c) an acid salt of a compound represented by formula (II) and (d) a water-soluble inorganic salt:

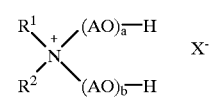

wherein $R^1$ represents a straight-chain or branched, alkyl or alkenyl group having 6 to 30 carbon atoms, $R^2$ represents a hydrogen atom, a methyl group or an ethyl group, AO may be the same or different from one another and each represents an oxyethylene group or an oxypropylene group, a and b each means an average value and is a number of 1 to 10 with the proviso that the total of a and b is from 2 to 15, and $X^-$ represents a counter ion; and

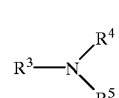

wherein $R^3$ represents a straight-chain or branched, alkyl or alkenyl group having 4 to 18 carbon atoms, and $R^4$ and $R^5$ may be the same or different from each other and each represents a hydrogen atom, a methyl group or an ethyl group.

* * * * *

UNITED STATES PATENT AND TRADEMARK OFFICE
CERTIFICATE OF CORRECTION

PATENT NO. : 6,030,923  
DATED : FEBRUARY 29, 2000  
INVENTOR(S) : OKANO ET AL.

PAGE 1 OF 2

It is certified that error appears in the above-identified patent and that said Letters Patent is hereby corrected as shown below:

In column 19, line 47 (claim 1), after "p and" please change "1" to -- q --.

In column 20, line 32 (claim 5), please change "alkyl" to -- ethyl --.

UNITED STATES PATENT AND TRADEMARK OFFICE
CERTIFICATE OF CORRECTION

PATENT NO. : 6,030,923
DATED : FEBRUARY 29, 2000
INVENTOR(S) : OKANO ET AL.

It is certified that error appears in the above-identified patent and that said Letters Patent is hereby corrected as shown below:

In column 19, line 47 (claim 1), after "p and" please change "1" to -- q --.

In column 20, line 32 (claim 5), please change "alkyl" to -- ethyl --.

Signed and Sealed this

Twenty-ninth Day of May, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO. : 6,030,923
DATED : February 29, 2000
INVENTOR(S) : Okano et al.

It is certified that error appears in the above-identified patent and that said Letters Patent is hereby corrected as shown below:

Column 19,
Line 47 (claim 1), after "p and" please change "1" to -- q --.

Column 20,
Line 32 (claim 5), please change "alkyl" to -- ethyl --.

Signed and Sealed this

Twenty-seventh Day of November, 2001

Attest:

NICHOLAS P. GODICI
*Attesting Officer*     *Acting Director of the United States Patent and Trademark Office*